United States Patent [19]

Löhn

[11] Patent Number: 4,515,564
[45] Date of Patent: May 7, 1985

[54] DENTAL HANDPIECE

[75] Inventor: Gerd Löhn, Biberach, Fed. Rep. of Germany

[73] Assignee: Kaltenbach & Voigt GmbH & Co., Fed. Rep. of Germany

[21] Appl. No.: 477,218

[22] Filed: Mar. 21, 1983

[30] Foreign Application Priority Data

Apr. 23, 1982 [DE] Fed. Rep. of Germany ....... 3215207

[51] Int. Cl.³ .............................................. A61C 1/08
[52] U.S. Cl. .................................................... 433/126
[58] Field of Search ................................ 433/126, 131

[56] References Cited

U.S. PATENT DOCUMENTS

| 4,080,737 | 3/1978 | Fleer | 433/126 |
| 4,332,562 | 1/1982 | Schuss et al. | 433/126 |
| 4,354,839 | 10/1982 | Schuss et al. | 433/126 |

FOREIGN PATENT DOCUMENTS

| 2929483 | 2/1981 | Fed. Rep. of Germany . |
| 1415787 | 11/1975 | United Kingdom . |
| 1535469 | 12/1978 | United Kingdom . |
| 1561227 | 2/1980 | United Kingdom . |
| 1563285 | 3/1980 | United Kingdom . |
| 1573712 | 8/1980 | United Kingdom . |
| 1573970 | 9/1980 | United Kingdom . |
| 2092450 | 8/1982 | United Kingdom . |

Primary Examiner—Robert Peshock
Attorney, Agent, or Firm—Scully, Scott, Murphy and Presser

[57] ABSTRACT

There is disclosed a dental handpiece which comprises a holder sleeve adapted to mount at one end a dental implement, a motor unit arranged in the sleeve, a power supply module releasably coupled to an opposite end of the sleeve and arranged to provide power to operate the motor unit, and a drive train extending within the sleeve from the motor unit to the dental-implement end of the sleeve to enable the motor unit to operate the dental implement. Fluid media supply lines are arranged inside the sleeve, but pass round the outside of the motor unit, and extend towards the implement-end of the sleeve in order to supply fluid media to the treatment region adjacent to the implement. The housing of the motor unit has a longitudinal groove in which the fluid media supply lines are taken, to achieve necessary guiding of the supply lines. The power supply module and the handpiece sleeve are freely rotatable relative to each other, when they are coupled together, by virtue of a guide pin and socket arrangement. The socket is provided by a coupling interpiece, and advantageously the coupling interpiece and the motor unit are interchangeably mounted in the handpiece. Desirably, the handpiece sleeve is transversely divided into two sleeve portions, and can receive a selected one of different interchangeable gear units.

26 Claims, 8 Drawing Figures

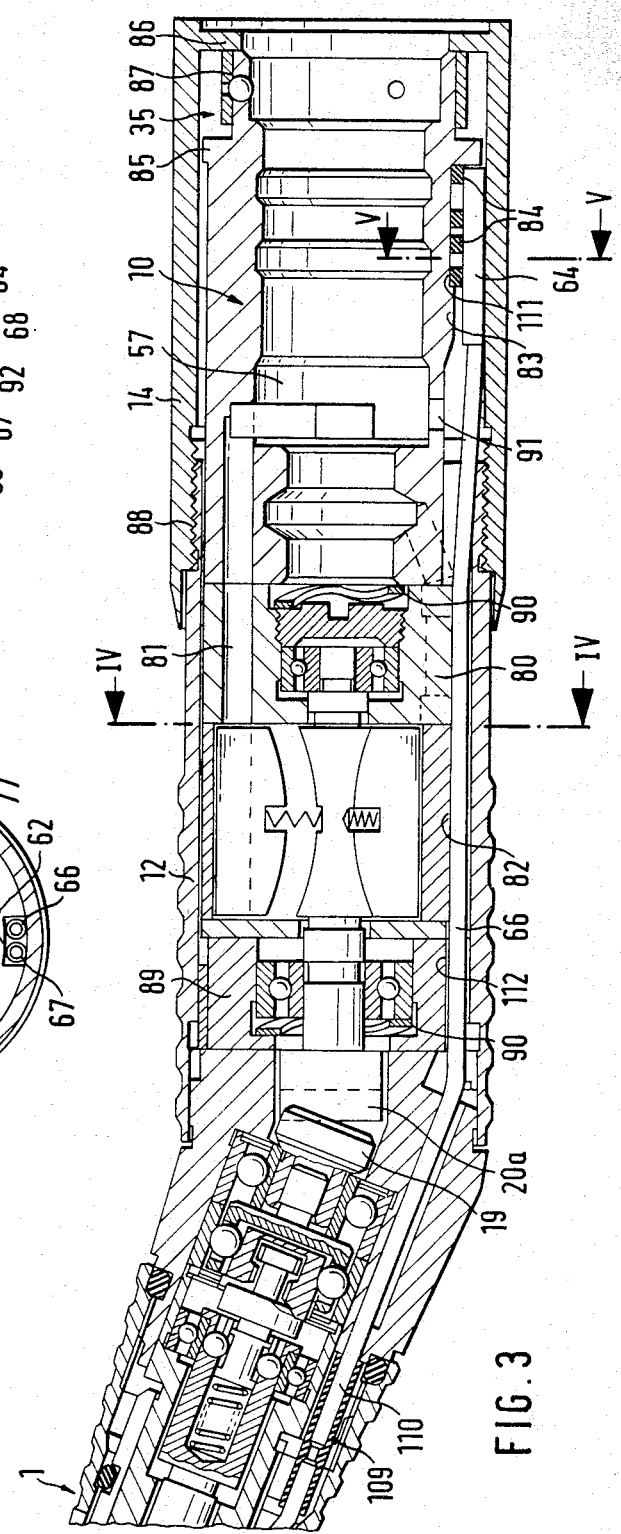
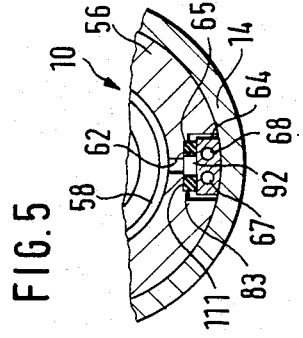
FIG.5
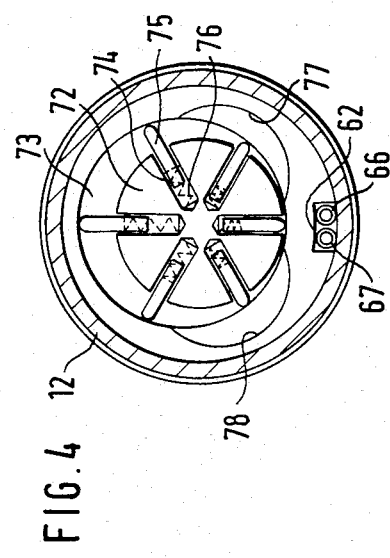
FIG.4
FIG.3

DENTAL HANDPIECE

TECHNICAL FIELD OF THE INVENTION

This invention relates to a dental handpiece comprising a handpiece housing, means provided at one end of the housing to mount a dental implement, a motor unit arranged in the housing, a power supply module releasably coupled to an opposite end of the handpiece housing and arranged to provide power to operate the motor unit, a drive train extending within the housing from the motor unit to said one end of the housing to enable the motor unit to operate the dental implement when the latter is mounted in the handpiece, and at least one supply line arranged to supply a fluid medium to a treatment region adjacent to the dental implement.

BRIEF DESCRIPTION OF THE PRIOR ART

Dental handpieces having the above general structure are known in many forms. Distinction is made in particular between air-driven handpieces (compare U.S. Pat. No. 3,439,422 and U.S. Pat. No. 3,349, 490) and electrically driven handpieces (compare DE-AS No. 12 34 922). A common factor of these embodiments is a drive device, on the one hand a multi-plate air motor and on the other hand an electric motor, which is integrated into a grip sleeve essentially the same in each case, the shaft of the motor serving to mechanically drive a drill by means of a shaft in the grip sleeve. A cooling medium supplied via a supply portion is conducted past the grip sleeve to the working area of the tool via an external line.

A disadvantage of these handpieces is that the arrangement of the individual elements is always appropriate for only one type of construction, i.e. in respect of power, speed, torque and a straight or angled handpiece. The cooling means lines are also awkwardly arranged externally, which makes handling of the known handpieces considerably more difficult. The external cooling means line can then also be damaged, which could interrupt the necessary cooling, which can be dangerous for the patient. Finally, in certain circumstance, it is advantageous to provide other supply lines, for example for measuring devices, for lighting purposes, etc., which would also have to be arranged externally like the cooling means supply lines. This complicates handling even further. Finally, the known handpieces are very long and therefore unwieldy, and corresponding tilting moments occur in the hand of a dentist when working is being carried out.

Apart, then, from the fact that the known dental handpieces are designed in each case only for one supply part and only for one type of work, there is the disadvantage that handling is difficult.

It is therefore the aim of the invention to develop a dental handpiece of the known type in such a way that handling it is made easier with a simple structure.

According to the invention there is provided a dental handpiece comprising a handpiece housing, means provided at one end of the housing to mount a dental implement, a motor unit arranged in the housing, a power supply module releasably coupled to an opposite end of the handpiece housing and arranged to provide power to operate the motor unit, a drive train extending within the housing from the motor unit to said one end of the housing to enable the motor unit to operate the dental implement when the latter is mounted in the handpiece, and at least one supply line arranged to supply a fluid medium to a treatment region adjacent to the dental instrument, in which:

the supply line is arranged to extend within the handpiece housing;

and the power supply module is freely rotatable relative to the handpiece housing when it is coupled therewith.

It has of course already been recognised that free rotatability of a handpiece holder sleeve relative to supply tube is advantageous for air-driven handpieces. A connecting piece insertable into the holder sleeve was therefore proposed (DE-GM No. 77 29 110) comprising radially directed outlet apertures and to whose frontal face the supply tube is couplable, in particular by means of a quick-coupling device. The problem mentioned in the introduction, does not, however, occur with this known handpiece, since the drive portion acts directly on the implement (tool), that is, it is arranged at the tool end of the sleeve. Cooling means lines, which can be provided, do not therefore have to be guided past the motor unit, and can therefore be arranged without any complications inside the sleeve, since sufficient space is available. If, however, the motor unit is in spaced arrangement from the tool, which is desirable for handling reasons, then the problem mentioned above does occur, and to overcome this supply media lines such as cooling means lines must be guided past the outside of the sleeve, in accordance with prior art.

According to preferred embodiments of the invention, there can be provided a dental handpiece, which is constructed and can be assembled in a simple manner, it being possible over and above this for the operator to work optimally regardless of the respective power supply available, and moreover in complete independence, as applicable, of whether a power supply module is provided and suitable for air-driven or electrically driven handpieces. Handling is much easier every time since external supply lines do not obstruct and since the handpiece housing e.g. a so-called grip sleeve with the tool is freely rotatable relative to the supply module and therefore relative to a power supply tube. A small and compact form is then achieved and all the transfer points for the media are arranged inside the grip sleeve area. Moreover, a rapid exchange of parts is possible as work is being carried out, as is optimal assembly. Thus, not only may cooling means and other fluid supply media be carried through in a simplified and integrated manner, but also signal lines, such as electrical lines, photoconductors, measuring lines and similar. Advantages in respect of compact structure and rapid assembly may be achieved if the grip sleeve is divided transversely and/or if the components in the grip sleeve are to a large extent interchangeable. This can be of particular advantage for the motor unit (drive part) and the part which is provided in the grip sleeve for connection to the supply tube. In addition, if the grip sleeve is transversely divided, an exchangeable gear unit may be provided for a through-drive, stepping-up or stepping-down transmission.

It should be mentioned in this context that the suggestion has already been made for an electric-motor-driven handpiece of providing a grip sleeve connected to the drive part comprising the drive motor, into which grip sleeve part a unit made up of the gearing and cam is axially and exchangeably insertable, an angled or a straight sleeve head optionally being couplable to this grip sleeve part (DE-AS No. 28 10 044). There are, however, no cooling means lines or other supply media lines for this known handpiece, consequently ideas for overcoming the above problem can not be given here either.

The invention is described in greater detail with the use of embodiments shown in the drawings. More particularly, the invention is described in detail with the use of an air-driven handpiece with an angled sleeve head.

BRIEF DESCRIPTION OF THE DRAWINGS

FIG. 3 is an enlarged view, similar to FIG. 2, of details of the first embodiment of the invention;

FIG. 4 is a section along IV—IV in FIG. 3;

FIG. 5 is a section along V—V in FIG. 3;

DESCRIPTION OF PREFERRED EMBODIMENTS OF THE INVENTION

Figure 1:
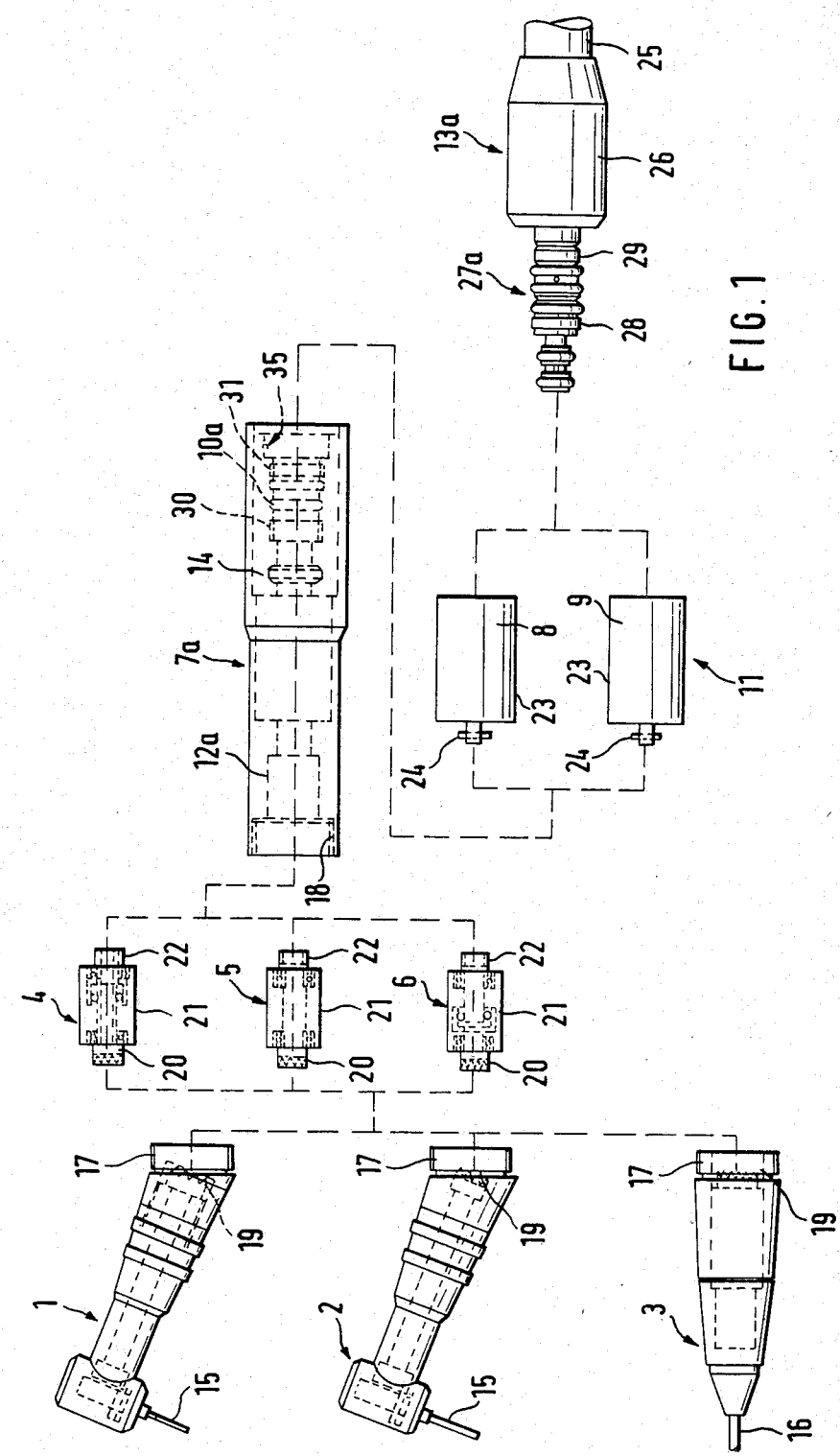
FIG. 1 is a schematic illustration of the basic structure of a dental handpiece according to the invention.

A unit construction method of assembly for a dental handpiece according to the invention first is described in greater detail with the use of FIG. 1. FIG. 1 shows different basic elements of this type of dental handpiece, and moreover an example of the invention is described further with the use of an embodiment with a transversely divided grip sleeve, namely grip sleeve parts at the tool end and the drive end.

FIG. 1 shows first of all three different tool end grip sleeve parts 1, 2 and 3 (parts which mount a dental implement), then three different gear parts 4, 5, 6, one drive-end grip sleeve part 7a, two different motor units 11, namely an air-motor catridge 8 and an electric motor cartridge 9, a coupling interpiece 10a, which is inserted in the grip sleeve part 7a, and a supply part 13a (power supply module).

The individual components are interchangeably connectable to each other in the ways shown by broken lines, whereby dental handpieces can be produced with different stepping-up and -down and different tool-end treatment parts and, as applicable, even a different type of power supply.

As shown schematically, the tool-end grip sleeve part 1 is an elbowed grip sleeve part, which has built into it at least one slide coupling, and if necessary a further gear near the coupling end. Elbow pieces of this type are known per se and conventional.

The tool-end grip sleeve part 2 comprises, as shown, an undivided, through-going drive shaft.

The two tool-end grip sleeve parts 1 and 2 act on interchangeable tools, namely drills 15.

The tool-end grip sleeve part 3 is designed for a so-called straight sleeve head and serves for example to drive a coaxial tool, such as a file 16, which is intended to carry out a to-and-fro movement along the axis and possibly a rocking movement around the axis. The tool end grip sleeve part 3 contains for this purpose a movement-conversion device, which is not shown in detail. Such grip sleeve parts are conventional and known per se, and therefore any further explanation would also appear to be unnecessary.

It should also be said that there are still many other tool-end grip sleeve parts, with which other tools for specific movements in each case can be driven, the grip sleeve parts being providable for angled sleeve heads and for straight sleeve heads.

The grip sleeve parts 1, 2, 3 at the tool end comprise in corresponding ways at the end facing the tool 15, 16 on the one hand a coupling element 17 for connecting to a coupling element 18 coacting uniquely therewith on the drive part of the grip sleeve 7a (respectively 7, 7b), and on the other hand an engaging part 19, such as frontal toothing on a drive shaft part for engaging with an engaging part 20 of a corresponding design on the drive shaft of a gear part 4, 5, 6.

Each of the gear parts 4, 5, 6 basically comprises a housing 21, which is essentially the same for all the gear parts 4, 5, 6, the output side engaging part 20 and a drive-side engaging part 22. The output-side engaging part 20 and the drive-side engaging part 22 are also essentially the same for all the gear parts 4, 5, 6. The different gear parts 4, 5, 6 differ in respect of their internal structure, namely in the respect of the relationship between drive-side and output-side speed. The shown gear parts 4 to 6 show the basic types, namely on the one hand a stepping-up gear part, on the other hand a through-drive gear part 5, and finally a stepping-down gear part 6.

Other gear parts can also be used apart from these, whose outer structure is the same as the gear parts 4 to 6, that is they have a housing 21, output-side engaging part 20 and drive-side engaging part 22, but which have different transmission ratios between the drive-side and the output side. Finally, slide couplings and other coupling elements can also be provided in the gear parts to prevent jerking or similar, as known per se.

The grip sleeve part at the drive end 7a shown in FIG. 1, or, in short, the drive grip sleeve part 7a, is distinguished by the fact that on the one hand each gear part 4, 5, 6 is insertable in a rotation-proof manner from the side with which the drive grip sleeve part 7a is connectable via its coupling element 18 to the tool-end grip sleeve part 1, 2, 3 by means of the latter's coupling element 17. Each gear part 4, 5, 6 is insertable into the drive grip sleeve part 7a in such a manner that when the tool-end grip sleeve part 1, 2 or 3 is coupled to the drive grip sleeve part 7a, the former's engaging part 19 is in engagement with the output-side engaging part 20 of each gear part 4, 5, respectively 6. The drive-side engaging part 22 of each gear part 4, 5, 6 is set in motion, i.e. rotated, in the drive grip sleeve part 7a by a further drive device described below.

In dental handpieces a basic distinction is made between a drive by means of a fluid, namely air in particular, and a drive by means of electric current. Both basic drive options can be used with the invention. At least two motor cartridges or similar are provided for this purpose as drive parts 11, of which one is a fluid motor, more particularly an air motor 8, and of which the other is an electric motor 9. As shown, both motors 8, 9 and, as appropriate, any other unit suitable as a drive part 11, have an essentially identical housing 23 and an output-side engaging part 24. The output-side engaging part 24 of each drive part 11 is designed so that it can come into rotational engagement with the drive-side engaging part 22 of each gear part 4, 5, 6. That is to say, the air motor 8 and the electric motor 9 each act on an output shaft, whose ends projecting towards the outside of the drive part 11 are designed essentially to form the engaging part 24. The drive grip sleeve part 7a is also designed so that each drive part 11 can be introduced from the other end, in such a way that, when inserted, it can come into rotational engagement via the output-side engagement part 24 with the drive-side engagement part 22 of the gear parts 4, 5, 6 (when they are inserted into the drive grip sleeve part 7a).

It is achieved in this way that, irrespective of the available supply system, the tool 15, respectively 16 can be driven in the desired manner and at the desired rate of revolutions or speed. It can be sufficient here if only one drive grip sleeve part 7a is available, regardless of whether the supply is a fluid supply or a current supply.

As will be explained further below, the dental handpiece can also be designed so that the drive part 11 acts directly on the drive-side engaging part 19 of the tool-end grip sleeve part 1, 2, 3 via its output-side engaging part 24, so that therefore no gear part is provided.

Should both choices be provided optionally, i.e. drive grip sleeve parts 7 and 7a are present, the output-side engaging part 24 of the drive part 11 and the output-side engaging part 20 of each gear part 4, 5, 6 are advantageously of an identical design and therefore each drive-side engaging part 19 of each tool-end grip sleeve part 1, 2, 3 and each drive-side engaging part 22 of each gear part 4, 5, 6 are also of the same design in a complementary fashion.

In order now to be able to conduct the power made available from the respective supply to the respective relevant drive part 11 (on the one hand air motor 8, on the other hand electric motor 9), coupled engagement is achieved between the drive grip sleeve part 7, respectively 7a, and a suitably designed supply part (13 or 13a), in such a manner that the supply part 13, 13a and grip sleeve part 7, 7a are freely rotatable relative to each other.

For this purpose, one of the two parts comprises a coupling interpiece and the other of the two parts a guide pin complementary thereto, both of which are of an essentially rotationally symmetrical design. This is illustrated with the air of an embodiment, in which the guide pin 27, 27a projects from the supply part 13, 13a, and in which a complementary coupling interpiece 10, respectively 10a, is built into the supply-part end of the drive grip sleeve part 7, respectively 7a. It must however, be said that the guide pin can of course also be provided on the grip sleeve part and the coupling interpiece in the supply part.

That is to say, the supply part 13, 13a is designed according to the principle of a plug part, whilst the grip sleeve part 7, 7a is designed according to the principle of a socket part.

The supply part 13, 13a basically comprises a tube 25, which contains all the necessary (and normal) supply lines such as for compressed air, cooling fluid, current, etc. At the end of the tube 25 facing the drive grip sleeve part 7, 7a, the supply part 13, 13a comprises a closing piece 26, which is not shown in detail, and whose external design is that of a grip part, with the aid of which the supply part 13, 13a can be coupled to the grip sleeve part 7, 7a. Connected to the frontal end of the tube 25, respectively the closing part 26, is a pinlike projection, in short a guide pin 27, respectively 27a. As will be explained below in detail, the guide pin 27, 27a comprises fluid outlets as connecting points which lie axially adjacent to each other and are separated from each other by seals. In the case of the embodiment shown in FIG. 1, the guid pin 27a also comprises electric, annular contacts (slip rings 28, respectively 29), in such a way that a supply is possible both with fluid and with electric current, so that, as shown in schematic representation in FIG. 1, both an air motor 8 and an electric motor 9 can be driven by means of this supply part 13a.

The drive grip sleeve part 7a contains in its interior a coupling interface 10a, which is designed to receive in coupling fashion the guide pin 27a of the supply part 13a, in such a way that the guide pin 27a and the drive grip sleeve part 7a are rotatable relative to each other as required, the fluid or respectively the electric current being able to be drawn off in a suitable manner in any position of rotation and fed to the appropriate drive part 11, or respectively as a cooling medium to the tool working area. This is effected in a manner described below. To supply the electric motor 9, the electric current is drawn off via the electric, annular contacts 28, 29 by means of other loop bodies such as slip rings 30 and 31 in the coupling interpiece 10. One of the two contact elements can then be under a flexible pretension.

The guide pin 27, 27a is designed to notch into the coupling interpiece 10, 10a, in such a way that when notched-in, a connection is achieved between the supply part 13, 13a and the grip sleeve part 7, 7a which is rigid but releasable by pulling.

It is important that the coupling interpiece be designed on the one hand to supply the various drive parts 11, but on the other hand for the purpose of couplable connection to a supply part. Suitable selection of the coupling interpiece permits any type of supply part to be used for driving the tools 15, 16, a specific drive part 11 being used in each case.

Figure 2:
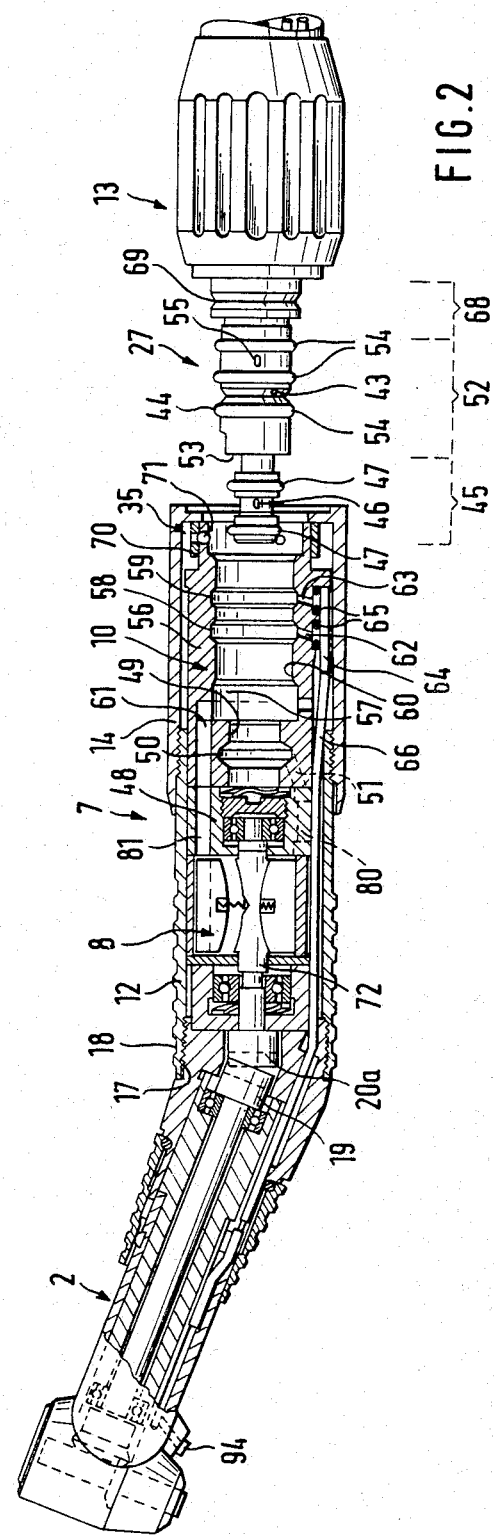
FIG. 2 is a schematic and detailed illustration of a first embodiment of the invention.

An example of the invention is described below in greater detail with the use of air-driven dental handpieces, i.e. with the use of handpieces containing an air motor 8 as a drive part 11. FIG. 2 shows an embodiment, in which the supply part 13 acts directly on the air motor 8 in the grip sleeve part 7 via the guide pin 27 and the coupling interpiece 10. FIG. 3 shows details of the coupling interpiece 10 and, in conjunction with FIG. 4, details of the air motor 8. The supply part 13 is distinguished from the supply part 13a according to FIG. 1 by the fact that there are no electrical contacts 28, 29, there being likewise no electrical contacts 30, 31 in the associated complementary coupling interpiece 10. Common to the embodiments according to FIGS. 2 and 3 is the fact that the air motor 8 acts via its output-side engaging part 20a directly on to a tool-end engaging part 19 of a tool-end grip sleeve part, on the one hand of the grip sleeve part 2 (FIG. 2) and on the other hand of the tool-end grip sleeve part 1 (FIG. 3). As can be seen from FIG. 3 and FIG. 4, the air motor 8 is a multi-vane motor, whose operating principle is known per se. According to the embodiment, not only is the power driving the respective part 11 (air for the air motor 8, respectively current for the electric motor 9) conducted via the respective supply part 13, respectively 13a and on to the tool working area, but also other media such as cooling fluid and signals such as electrical or light signals, and also illuminating power. It should also be said that the respective drive part (air motor 8 and electric motor 9) can also be designed in such a way (not shown), that the drive part 11 can be cooled by means of supplied cooling fluid, as known per se (cf. DE-PS No. 12 34 922).

The embodiment according to FIG. 2 shows an embodiment for the supply and removal of air as well as the supply of cooling fluid and removal of cooling air. The supply part 13 comprises a guide pin 27, which has the outlet apertures for the different media. The coupling interpiece 10 is then of an appropriate design. Details of the coupling interpiece 10 are given in FIG. 3. The front end of the guide pin 27 has a section 45 of a smaller diameter, which has a radial aperture 46 for air supply. Mounted on both sides of this aperture 46 in axially spaced arrangement on the section 45 are annular seals 47 or O-rings, which are for example disposed in grooves (not shown). The socket-like coupling interpiece 10 has, in a complementary manner, a section 48 with an inner bore 49 of a smaller diameter at its front end facing the air motor 8. An annular groove 50 is provided roughly centrally in the inner bore 49. The annular groove 50 comprises a connection 51 for the corresponding connection to the air motor 8, which has yet to be described.

When the supply part 13 is inserted into the coupling interpiece 10 (cf. also FIG. 6), the aperture 46 is aligned with the annular groove 50 and the annular seals 47 off outwardly the space of the annular groove 50 by virtue of the fact that they abut the inner wall of the inner bore 49 on both sides of the annular groove. The air supply can then be conducted via the connection 51 to the air motor 8 to drive it.

A central section 52 of the guide pin 27 has on its frontal side, i.e. on the annular surface 53 facing the front section 45 an unshown aperture for the removal of air. This air-removal aperture can also be provided on the connected cylindrical section. Abutting this, three annular seals 54 or O-rings are mounted on the central section 52, which separate areas of the section 52 from each other, in which apertures for the cooling fluid and the cooling are provided, namely on the one hand the aperture 43 in an annular groove 44 and on the other hand the aperture 55.

The coupling interpiece 10 also has a central section 56 in a complementary fashion, whose end facing the front section 48 has a radial bulge 57 and which has further along it two annular grooves 58 and 59. The diameter of the bulge 57 and of the annular groove 58 and 59 is greater than the inner diameter of the inner bore 60 associated with the central section 56. When the guide pin 27 of the supply part 13 is inserted into the coupling interpiece 10, the annular seals 54 seal and divide the bulge 57 from the annular grooves 58 and 59 and the two annular grooves 58 and 59 from each other in each case on both sides of the annular grooves 58 and 59, by virtue of the fact that they border on the inner bore 60.

The bulge 57 is connected via an essentially axial connection 61 to a corresponding removal line of the air motor 8 which is yet to be described. Similarly, the annular grooves 58 and 59 are connected via connections 62, respectively 63 to line terminals, which in the case of the shown embodiment are combined to form a single line terminal 64. The passage between the connections 62 and 63 and the associated line terminal 64 is effected in a sealed manner with the aid of seals 65, more particularly annular seals such as O-rings. Tube lines 66, respectively 67 are connected to the line terminal 64, which are connected in each case to one of the connections namely 62 or 63 and which permit a connection and thus a supply of cooling air, respectively cooling fluid to the tool working area, as will be explained below.

The guide pin 27 has connected to the central section 52 another rear section 68 of a larger diameter, which comprises an annular groove 69. Complementary thereto, the coupling interpiece 10 has a rear section for the locking device 35, having peripherally distributed locking members, namely locking spheres 71, which are designed to engage into the annular locking groove 69 of the guide pin 27. When inserted into the coupling interpiece 10, the supply part 13 is retained by the locking spheres 71 locking into the annular locking groove 69, with counter-pressure from an arcuate spring 70, which outwardly encloses the locking spheres 71, which are inserted into apertures 87 in the section of the coupling interpiece 10 complementary to the section 78, and project over a portion inwardly beyond it. The guide pin 27 is thereby retained in the coupling interpiece 10. The remaining parts can be supplied with and relieved of supply air, cooling fluid and cooling air, and removal is possible in any position of rotation of the supply part 13 (cf. also FIG. 6). The guide pin 27 can be released from the coupling interpiece 10 in a simple manner by axial pulling, by virtue of the fact that the locking spheres 71 are pushed radially outwards against the force of the spring 70 and leave the annular locking groove 69 in the guide pin 27.

The air motor 8 is designed as a multi-vane motor in a way known per se. It comprises (cf. particularly FIGS. 3, 4 and 7) a central shaft 72, which is rotatable in a circular compartment 73 displaced relative to the centre. The shaft 72 comprises radial slots 74, into which plates 75 are pushed radially outwards into abutement on the inner wall of the compartment 73 by the force of a spring 76. Air is supplied in a somewhat displaced manner relative to the point at which the shaft 72 is closest to the inner wall of the compartment 73, which air acts on the plates 75 and rotates these together with the shaft 72, the supplied air then leaving the inner compartment 73 at the point where there is the greatest distance between the shaft 72 and inner wall of the inner compartment 73. According to which side of the point of closest vicinity air is supplied to, there follows a right- or left-handed rotation of the shaft 72. The air motor 8 is designed in a way known per se such that the air can be fed to the inner compartment 73 both to the right and left of the point of closest vicinity, the supply being effected optionally to the right or the left. For this purpose, the air motor 8 comprises a first supply aperture 77 and a second supply aperture 78, the aperture 77 being provided in the representation according to FIG. 5 for rotation in a counter-clockwise direction, and the aperture 78 for rotation in a clockwise direction. According in each case to the angle position of the coupling interpiece 10 relative to the air motor 8, either the aperture 77 or the aperture 78 will coact via the connection 51 in the coupling piece 10 and a connection 79, respectively 80, in each case aligned therewith (cf. also FIG. 8), of which one is linked with the first aperture 77 and the other with the other aperture 78. The end of the inner compartment 73 having the greatest distance is linked via a connection 81 to the connection 61 in the coupling interpiece 10, regardless of the respective angle position, in such a manner that a removal of the air from the inner compartment 73 is always ensured. It must, however, be emphasised that the invention is also applicable to air motors which are not operable in both directions of rotation, in which case then only one of the connections 79 or 80 need be provided.

The air motor 8 (likewise a corresponding electric motor 9) also comprises a through-passage in the form of a longitudinal groove 82 for the cooling means tube lines 66 and 67. Since the supply of cooling means should be independent of the angle position of the coupling interpiece 10 and therefore of the direction of rotation of the motor, the tube lines 66 and 67, as appropriate, between the line terminal 64 on the coupling interpiece 10 and their continuation towards the tool end working area are designed in such a way that the connection of media is guaranteed regardless of the angle position of the coupling interpiece 10.

A reliable connection of the cooling means tube lines 66, 67 over the frontal end of the drive grip sleeve part 7 out towards the tool-end grip sleeve part 1, respectively 2, respectively 3, must also be guaranteed so that the cooling means can escape safely from outflow apertures such as the outflow aperture 94 (FIG. 2) to the tool working area. This is achieved by the fact that the connecting lines for the cooling means are designed as tube lines, which are secured in the tool-end grip sleeve part 1, respectively 2, respectively 3, i.e. they project from this towards the drive grip sleeve part 7. This can be achieved for example by a sleeve 109 linked to the outlet end 94 being provided in the tool-end grip sleeve part (cf. FIG. 3), in which sleeve 109 the tool-end 110 of the tube line 66 is insertable, a similar arrangement being provided for the tube line 67, which runs essentially parallel thereto. It should also be said that the shaft 72 of the air motor 8 (similarly to a corresponding shaft of the electric motor 9) is mounted and axially supported by spring annuli 90 in the housing 23 in a manner known per se, in order in this way to be able better to absorb tolerances in the axial dimensions.

Figure 6:
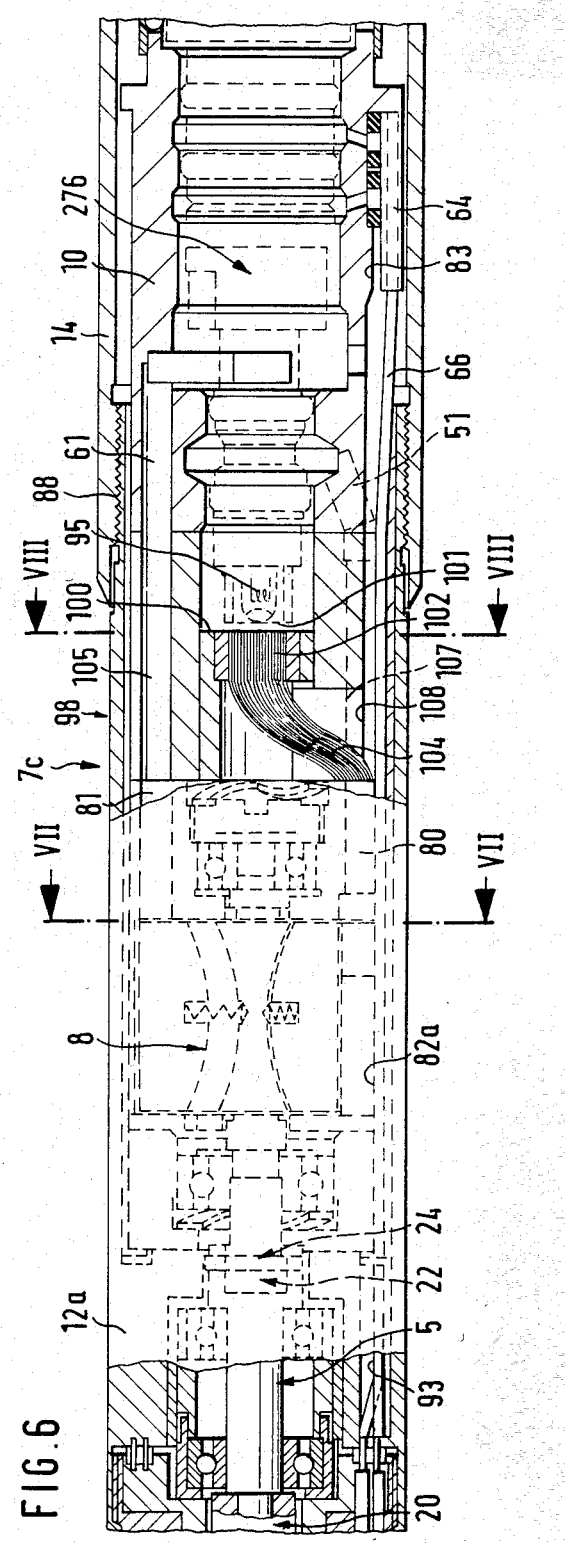
FIG. 6 is a view of a further embodiment of the invention, in a section similar to FIG. 3.

As can be seen in FIG. 6, the engaging part 24 of the air motor 8 can consist of a follower pin diametrically penetrating the shaft butt, which pin engages into a diametrical slot of a shaft projection of the corresponding engaging part of a gear part 5. On the other hand, the engaging part 20 (FIG. 6) on the gear part 5, respectively the engaging part 20a (FIG. 3) on the air motor 8, has the form of a spur gear, thereby permitting engagement into a correspondingly designed engaging part 19 of a tool-end grip sleeve part 1, 2 or 3, drive engagement thus being achievable both for angled and straight tool-end grip sleeve parts. FIG. 3 shows a coupling and gear unit which is otherwise normal in itself and is not described in any greater detail, and on which the engaging part 19 acts.

As mentioned, a supply part with electric conductors can be connected in principally the same way for example by means of slip rings 28, 29, respectively slip bodies 30, 31 (cf. FIG. 1).

Signal lines can also be provided in the same way as for the cooling means tube lines 66, 67, in order to transfer for example electrical or optical signals to the working area, or respectively to transfer from here to the supply part.

Figure 8:
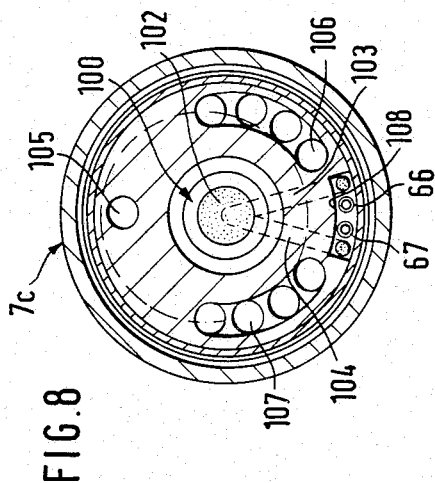
FIG. 8 is a section along VIII—VIII in FIG. 6.
Figure 7:
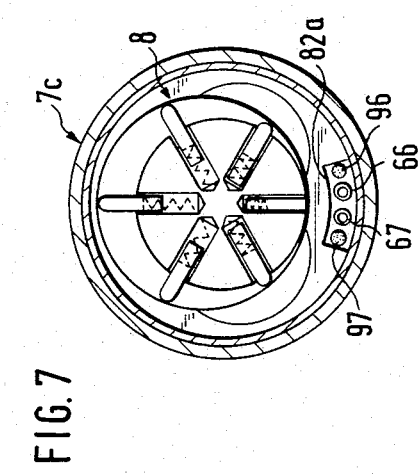
FIG. 7 is a section along VII—VII in FIG. 6.

FIGS. 6 to 8 show a particular embodiment in which the light signals can be conducted from the supply part to the working area.

The supply part of the embodiment according to FIG. 6 corresponds in all the essential details to that according to FIG. 2 and therefore to that which can also be used according to the embodiment shown in FIG. 3. It can therefore be inserted into a coupling interpiece 10, as already explained.

The supply part according to FIG. 6 differs from that already described, however, in that a light-emitting device is provided on the frontal end 101 of the section 45 of the guide pin 27b. This is formed in the shown embodiment by a lamp 95. It can also be a light-emitting diode (LED) or similar. The frontal face of a photoconductor can also possibly form this light-emitting device. Since, on the other hand, the drive parts 11 used in each case (air motor 8, respectively electric motor 9) take up a considerable and essentially central area, the light signals must be conducted past these, similarly to the cooling means tube lines 66, 67. That is to say, as shown in FIG. 7, not only are the tube lines 66 and 67 arranged in the longitudinal groove 82a, but also corresponding light-transmitting conductors, namely photoconductors 96 and 97. Similarly to the case of the cooling means, supply of the light signals from the photoconductors 96, 97 to corresponding photoconductors in the tool-end grip sleeve part 1, 2, respectively 3, is effected by means of an arrangement as already described for the tube lines with the use of FIG. 3.

It is also important that the light signals are transferred from the roughly axially arranged lamp 95 as a light source to the photoconductors 96 and 97, which are provided in the longitudinal groove 82a on the outer edge of the grip sleeve part 7.

This can be done in a manner in principle similar to that described for the fluid lines, respectively for the loop ring connections for electric contacts. The shown embodiment is, however, advantageous. Here, an interpiece 98 is additionally inserted between the selected drive part 11 and the selected coupling interpiece 10 into the drive grip sleeve part 7. In the centre the interpiece 98 comprises a photoconductor 102 arranged in a frontal wall 100 and lying in directly opposite arrangement, with slight spacing, to the lamp 95 when the guide pin 27b is inserted into the coupling interpiece 10, this photoconductor being divided in the shown embodiment into two strands or bundles 103 and 104 (cf. FIG. 8), which transfer towards the exterior into the photoconductors 96, respectively 97 in the longitudinal groove 82a of the air motor 8, for example via appropriate (unshown) coupling pieces. Of course, transfers are also possible correspondingly in respect of other signal lines.

It is also important for the interpiece 98 that corresponding connections 105 are provided between the connections 61 and 81 and 106, respectively 107 between the connection 51 and the apertures 77, respectively 78. A longitudinal groove 108 is of course also provided, which has the same task as the longitudinal groove 82a in the air motor 8, i.e. to receive the cooling means tube lines 66, 67 and/or other signal lines.

This shows, then, that the drive grip sleeve part 7c of this embodiment must have different dimensions in an axial direction from the grip sleeve part 7a or 7 of the previously described embodiments, in order to be able in addition to receive the interpiece 98.

The drive grip sleeve part therefore consists advantageously of two sleeve sections 12, respectively 12a and 14 connected to each other by means of a thread 88.

The tool-end sleeve section 12, respectively 12a of the grip sleeve part is advantageously designed to receive the respective drive parts 11, and the interpiece 98 and the respective gear part 4–6 as necessary, whilst the rear, supply part-end sleeve section 14 of the grip sleeve part is designed to receive the respective corresponding coupling interpiece 10, advantageously including the locking device 35.

For this purpose, the coupling interpiece 10 on the one hand has in the area of the locking device 35 an end collar 85 with an outer diameter corresponding to the inner diameter of the sleeve part 14, and the sleeve section on the other hand also has at its end, i.e. at the supply part end, an end collar 86, against which the coupling interpiece 10 comes into abutment, in the shown embodiment via the locking device 35.

As mentioned, a fluid-tight connection is provided between the coupling piece 10 on the one hand and the supply tube lines 66, 67 on the other hand, as can be seen particularly from the sectional view in FIG. 5. The tube supply lines 66, 67 are bedded into the line terminal 64, for example soldered or cast in another way, and are linked, as shown for the tube line 68, to the side of the line terminal 64 facing the axis of the arrangement via an aperture 92. The longitudinal groove 83 of the coupling interpiece 10 is matched in the area of the line terminal 64 to the latter's outer form and has a depression 111 opposite the apertures 92, into which the respective annular seal 84 is inserted. The side of the line terminal 64 facing the inner wall of the sleeve section 14 is rounded off to match the pattern of this section. The supply part end advantageously abuts the end collar 85 of the coupling interpiece 10.

A safe, fluid-tight connection is guaranteed in this way between the roughly radial through-passages 62, respectively 63 and the associated tube line 68, respectively 67 via the line terminal 64.

There is also provided between the longitudinal groove 83 and the bulge 57 in the coupling interpiece 10 forming the annular channel a connection 91, through which the leakage air from the air motor 8 can be fed back again.

It should also be noted that the drive part can also be of a multi-part design, in the case of the embodiment shown in FIG. 3, the air motor 8 consists of several parts connected to each other by means of the shaft 72 and bearings, but the annular part 89, for example, can be of a divided design, but then of course must likewise have a longitudinal groove 112 corresponding to the longitudinal groove 82. This annular part 89 can also comprise guide elements with projections, which engage into corresponding complementary guide elements such as depressions of the tool-end grip sleeve part, in this case the tool-end grip sleeve part 1 on its engaging element 17 (not shown in detail).

Finally, the individual parts are preferably provide with externally visible markings, from which the operator can draw conclusions as to their respective applicability or use.

It is thus shown that the dental handpiece designed according to the invention has considerable advantages in practice. It has a small, compact structure without any external supply lines for cooling means or similar, whereby easier manipulation is achieved on the basis of a more simple holding technique. Free rotatability between the supply part and grip sleeve is also guaranteed, and the coupling process can be carried out very quickly.

Other embodiments are of course also possible, within the scope of the appended claims.

I claim:

1. A dental handpiece comprising a universal holder sleeve member providing for the universal mounting therein of different types of motor units and drive trains, means provided at one end of the sleeve member to mount a dental implement, an interchangeable motor unit, interchangeable between electric motor units and pneumatic motor units, arranged in the sleeve member, a power supply member releasably coupled to an opposite end of the sleeve member and arranged to provide power to operate the selected motor unit, an interchangeable drive train, interchangeable between different gearing ratios, extending within the sleeve member from the motor unit to said one end of the sleeve member to enable the motor unit to operate the dental implement when the latter is mounted in the handpiece, at least one supply line extending within the sleeve member and arranged to supply a fluid medium to a treatment region adjacent to the dental implement, a socket provided in one of said members, a generally cylindrical guide pin provided on the other of said members to be received by the socket in a freely rotatable manner when the members are coupled together, and a power supply line extending from the power supply member to the motor unit via said pin and said socket, said guide pin and socket having a plurality of axially spaced rotational fluid connections therebetween, with a plurality of axially spaced sealing rings being provided for fluid sealing of the rotational fluid connections, and said guide pin and socket also having a plurality of axially spaced slip rings and associated electrical contacts thereon to also provide for rotational, electrically insulated electrical connections, with the rotational fluid connections and rotational electrical connections providing for connections to different types of motor units and dental implements.

2. A dental handpiece according to claim 2, in which said fluid medium supply lines and said power supply lines extend in axially distributed connection to the periphery of the guide pin with mutual spacing, and the socket has axially distributed connecting points, leaving mutual spacing, and corresponding to the connections of lines to the guide pin, said connecting points of the socket being connected to axis-parallel power and fluid medium supply lines and one connecting point forming outlet connections and the other forming inlet connections;

in which the outlet points and/or the inlet points are circular and axially spaced, and axial separation between the power supply line and the fluid medium supply line is provided between the axially spaced outlet and inlet points;

and in which the guide pin and the socket are rigidly interengageable in a complementary formation of an appropriate defined position.

3. A dental handpiece according to claim 2, including annular seals arranged on both sides of said outlet and inlet points in grooves provided in one of said guide pin and said socket, and engageable, when the guide pin and socket are interengaged, with the other of the guide pin and the socket.

4. A dental handpiece according to claim 3, in which the power supply line is capable of transmitting electrical power, and said seals comprise electrical insulation.

5. A dental handpiece according to claim 2, in which at least one of said connections is for a fluid medium and is formed by an annular channel into which opens approximately radially a respective fluid medium line at a respective connection point.

6. A dental handpiece according to claim 2, in which at least one of said connections is for electrical current and is provided by mutually contacting slip rings connected to respective connecting lines.

7. A dental handpiece according to claim 1, including interengageable latch members provided on the guide pin and the socket to define a specific latched position when the pin and the socket are coupled together.

8. A dental handpiece according to claim 7, in which the interengageable latch members comprise an annular locking channel and a latching element spring-loaded towards latching engagement with the locking channel.

9. A dental handpiece according to claim 8, in which the annular locking channel is provided on an end of the guide pin furthest away from the socket, and the latching element is mounted on an end of the socket which is closest to the guide pin.

10. A dental handpiece according to claim 1, in which the diameter decreases in steps towards the free end of the guide pin.

11. A dental handpiece according to claim 1, in which the guide pin is connected to an end of the power supply member which faces the sleeve member, and the socket is formed by a coupling interpiece fitted in an end of the sleeve member which faces the power supply member.

12. A dental handpiece according to claim 1, in which the coupling interpiece comprises a separate component which is inserted into the end of the free member.

13. A dental handpiece according to claim 1, in which the motor unit has a substantially cylindrical housing and includes connection lines associated therewith, such connection lines being in alignment with corresponding connection lines in the coupling interpiece.

14. A dental handpiece according to claim 1, in which the supply line for a fluid medium extends through the motor unit.

15. A dental handpiece according to claim 13, in which the motor unit is inserted as a separate component into the sleeve member.

16. A dental handpiece according to claim 15, including guide means for guiding the insertion of the motor unit into the sleeve member so that, upon insertion, the respective connection lines are aligned with each other.

17. A dental handpiece according to claim 16, in which the guide means comprises at least one guide tube for conveying a fluid medium to said treatment region and secured to the sleeve member, and an aligned axially extending longitudinal groove in the outer periphery of the motor housing which receives said tube.

18. A dental handpiece according to claim 17, including more than one said guide tube to be received by said longitudinal groove, a common line terminal piece, and means connecting said guide tubes to said common line terminal piece in such a way that individual currents of fluid medium are separated from each other.

19. A dental handpiece according to claim 18, including an annular seal arranged to separate fluid media between said common line terminal and connection points opening into said longitudinal groove.

20. A dental handpiece according to claim 11, including a photoconductor supply line for transmitting light to the dental treatment region and arranged to open centrally and coaxially to a free end face of the guide pin, and also centrally and co-axially to an end face of said coupling interpiece adjacent to said free end face of the guide pin.

21. A dental handpiece according to claim 20, including a longitudinal groove arranged in said sleeve member, in which said fluid medium supply line and said photoconductor supply line are received.

22. A dental handpiece according to claim 20, in which the photoconductor supply line is split, within the sleeve member, into a plurality of separate bundles of fibres.

23. A dental handpiece according to claim 1, including a dental implement-mounting portion and a motor-mounting portion which are connectible together to form said handpiece housing, complementary engaging elements provided on said portions to transmit drive along said drive train, and complementary coupling elements arranged on said portions to provide a rigid but releasable connection between said portions of the handpiece housing.

24. A dental handpiece according to claim 23, including a gear drive unit arranged in said handpiece housing to be driven by the motor unit in order to transmit drive to the drive train.

25. A dental handpiece according to claim 24, in which said gear drive unit is insertable as a separate component into said motor-mounting portion of the handpiece sleeve.

26. A dental handpiece according to claim 1, including first and second sleeves releasably connected together to form part of said sleeve member, said first sleeve being located closer to the dental-implement end of the handpiece and mounting therein said motor unit, and said second sleeve mounting therein said socket, and said motor unit and said socket being alignable with each other in fluid-tight manner when the first and second sleeves are connected together.

* * * * *

UNITED STATES PATENT OFFICE
CERTIFICATE OF CORRECTION

Patent No. 4,515,564   Dated May 7, 1985

Inventor(s) Gerd Lohn

It is certified that error appears in the above-identified patent and that said Letters Patent are hereby corrected as shown below:

Column 1, line 43: "circumstance" should be --circumstances--;

Column 5, line 41: "air" should be --aid--; and

Column 12, Claim 2: "...according to Claim 2" should be --...according to Claim 1--.

Signed and Sealed this

*Twenty-fourth* Day of *September 1985*

[SEAL]

Attest:

Attesting Officer

DONALD J. QUIGG

*Commissioner of Patents and Trademarks—Designate*